(12) United States Patent
Ito

(10) Patent No.: US 9,182,339 B2
(45) Date of Patent: Nov. 10, 2015

(54) CALIBRATION APPARATUS AND CALIBRATION METHOD

(71) Applicant: OLYMPUS CORPORATION, Tokyo (JP)

(72) Inventor: Ryosuke Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/202,240

(22) Filed: Mar. 10, 2014

(65) Prior Publication Data

US 2014/0185036 A1 Jul. 3, 2014

Related U.S. Application Data

(63) Continuation of application No. PCT/JP2012/074096, filed on Sep. 20, 2012.

(60) Provisional application No. 61/536,736, filed on Sep. 20, 2011.

(51) Int. Cl.
| | |
|---|---|
| *G01N 21/00* | (2006.01) |
| *G01N 21/17* | (2006.01) |
| *A61B 1/00* | (2006.01) |
| *G01N 21/27* | (2006.01) |
| *A61B 5/00* | (2006.01) |

(52) U.S. Cl.
CPC ............ *G01N 21/17* (2013.01); *A61B 1/00057* (2013.01); *A61B 1/00165* (2013.01); *A61B 5/0075* (2013.01); *G01N 21/274* (2013.01); *A61B 2560/0238* (2013.01)

(58) Field of Classification Search
CPC .............. G01J 3/02; G01J 3/51; G01J 3/513; G01N 21/65; G01N 15/1459

USPC .................................................. 356/300–445
See application file for complete search history.

(56) References Cited

U.S. PATENT DOCUMENTS

| | | | |
|---|---|---|---|
| 5,652,810 A * | 7/1997 | Tipton et al. | ..... 385/12 |
| 2002/0097400 A1 | 7/2002 | Jung et al. | |

(Continued)

FOREIGN PATENT DOCUMENTS

| | | |
|---|---|---|
| EP | 2 412 294 A1 | 2/2012 |
| JP | A-2009/537014 | 10/2009 |
| JP | A-2010-220894 | 10/2010 |

OTHER PUBLICATIONS

Kim et al., "Low-Coherence Enhanced Backscattering: Review of Principles and Applications for Colon Cancer Screening," *Journal of Biomedical Optics*, Jul./Aug. 2006 vol. 11, No. 4, pp. 041125-1- 041125-10.

(Continued)

*Primary Examiner* — Abdullahi Nur
(74) *Attorney, Agent, or Firm* — Oliff PLC

(57) ABSTRACT

A calibration apparatus includes an insertion portion into which a measurement probe is inserted and a reference reflection plate that is arranged at a position away from a distal end of the measurement probe by a predetermined distance in a state in which the measurement probe has been inserted in the insertion portion and that has uniform reflectivity of light in a range of a wavelength to be measured in an irradiation plane of an illumination light, wherein a material forming the reference reflection plate has a scattering mean free path that is greater than a spatial coherence length at the predetermined distance.

10 Claims, 18 Drawing Sheets

(56) References Cited

U.S. PATENT DOCUMENTS

2009/0009759 A1      1/2009   Backman et al.
2012/0170026 A1*     7/2012   Wilcken .......................... 356/51

OTHER PUBLICATIONS

Turzhitsky et al., "Characterization of Light Transport in Scattering Media at Subdiffusion Length Scales with Low-Coherence Enhanced Backscattering," *IEEE Journal of Selected Topics in Quantum Electronics*, May/Jun. 2010, vol. 16, No. 3, pp. 619-626.

Roy et al., "Association Between Rectal Optical Signatures and Colonic Neoplasia: Potential Applications for Screening," *Cancer Res*, May 15, 2009, vol. 69, 10, pp. 4476-4483.

International Search Report issued in International Patent Application No. PCT/JP2012/074096 dated Dec. 18, 2012.

Feb. 16, 2015 Extended Search Report issued in European Application No. 12833882.9.

* cited by examiner

FIG.20
(a)
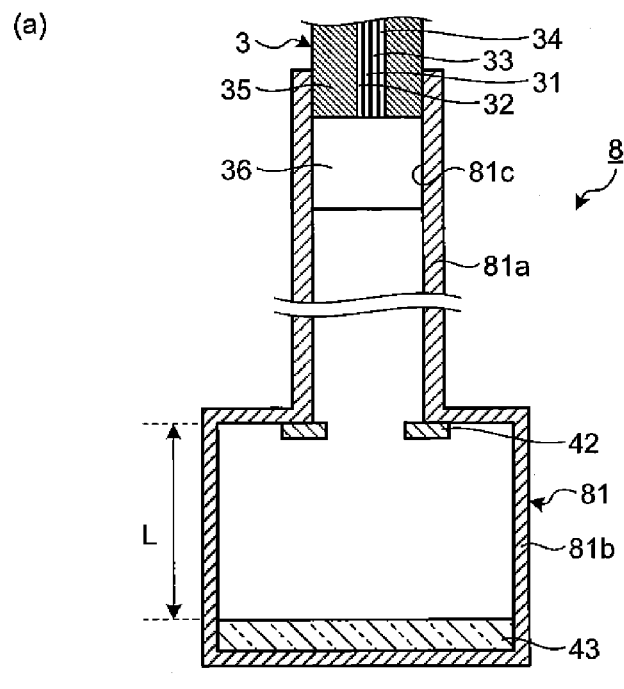
(b)
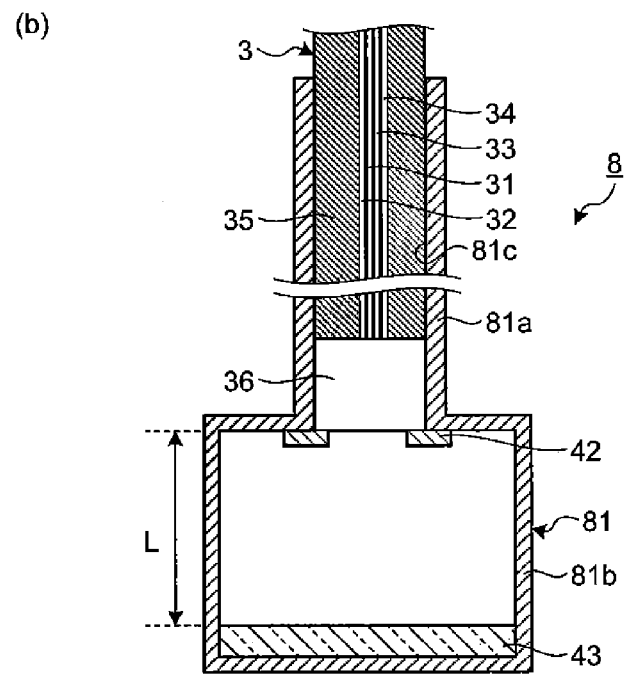

CALIBRATION APPARATUS AND CALIBRATION METHOD

CROSS-REFERENCE TO RELATED APPLICATIONS

This application is a continuation of International Application No. PCT/JP2012/074096, designating the United States and filed on Sep. 20, 2012 which claims the benefit of priority from U.S. provisional application No. 61/536,736 filed on Sep. 20, 2011, and the entire contents of the International application and the United States provisional application are incorporated herein by reference.

BACKGROUND OF THE INVENTION

1. Field of the Invention

The present invention relates to a calibration apparatus and a calibration method that calibrate an optical measurement apparatus that measures, as an amount of scattering and absorption of light, information related to an internal structure of an object to be measured.

2. Description of the Related Art

Conventionally, backward scattered returned light from a comparatively weak scattering medium such as body tissue has been known to be observed as light that increases interference according to a degree of spatial coherence of illumination light thereof (see Young L. Kim, et. al: Low-Coherence Enhanced Backscattering; Review of Principles and Applications for Colon Cancer Screening, Journal of Biomedical Optics, 11(4), 041125 2006). A technique of measuring spectroscopic information using this phenomenon is called low-enhanced backscattering spectroscopy (LEBS), and characteristics of an interference pattern with respect to a scattering mean free path (a reciprocal of a scattering coefficient) in a scattering medium have been well studied (see V, Turzhitsky, et. al: Characterization of Light Transport in Scattering Media at Subdiffusion Length Scales with Low-Coherence Enhanced Backscattering, IEEE journal of selected topics in quantum electronics, Vol. 16, No. 3, 619 (2010)). This scattering mean free path has a correlation with an internal structural change in the scattering medium and is used in detecting a minute tissue structural change as seen in early cancer. For example, distinguishment of colorectal cancer using an interference pattern of scattered returned light has been known to be possible (see Hemant K. Roy, et. al: Association Between Rectal Optical Signatures and Colonic Neoplasia: Potential Applications for Screening, Cancer Research, 69(10), 4476 (2009)).

A technique of applying the above mentioned LEBS to noninvasive measurement within a body through a small diameter probe inserted in an endoscope is known (see U.S. Patent Application Publication No. 2009/0009759). In this technique, in order to obtain an interference pattern, detection fibers are arranged at different plural positions in a plane on which the interference pattern is formed, and signals are detected by detectors corresponding to the respective detection fibers.

SUMMARY OF THE INVENTION

A calibration apparatus according to one aspect of the present invention obtains a plurality of calibration data used when an optical measurement apparatus corrects returned light from an object to be measured, the optical measurement apparatus including: a measurement probe having an illumination fiber that irradiates to the object to be measured illumination light including at least light of wavelength to be measured and a plurality of detection fibers that receive the returned light, which is of the illumination light reflected and/or scattered by the object to be measured; and a plurality of detection units that detect the returned light respectively received by the plurality of detection fibers, and the calibration apparatus includes: an insertion portion into which the measurement probe is inserted; and a reference reflection plate that is arranged at a position away from a distal end of the measurement probe by a predetermined distance in a state in which the measurement probe has been inserted in the insertion portion and that has uniform reflectivity of light in a range of the wavelength to be measured in an irradiation plane of the illumination light, wherein a material forming the reference reflection plate has a scattering mean free path that is greater than a spatial coherence length at the predetermined distance.

A calibration method according to another aspect of the present invention of obtaining calibration data using a calibration apparatus with respect to an optical measurement apparatus that includes: a measurement probe having an illumination fiber that irradiates to an object to be measured illumination light including at least light of wavelength to be measured and a plurality of detection fibers that receive, at different angles, returned light of the illumination light reflected and/or scattered by the object to be measured; and a plurality of detection units that detect the returned light respectively received by the plurality of detection fibers, includes: a first step of obtaining data for internal reflection calibration of the measurement probe detected by the detection units when the measurement probe is caused to irradiate the illumination light to an insertion portion that is provided, inside the calibration apparatus, with a light absorption member that absorbs light; and a second step of obtaining reference reflection plate calibration data detected by the detection units when the measurement probe irradiates the illumination light to a reference reflection plate in the calibration apparatus, the reference reflection plate being arranged at a position away from a distal end of the measurement probe by a predetermined distance and having uniform reflectivity of light over a range of the wavelength to be measured in an irradiation plane of the illumination light, wherein a material forming the reference reflection plate has a scattering mean free path that is greater than a spatial coherence length at the predetermined distance.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 20 is a diagram schematically illustrating an outline of a calibration process executed by an optical measurement apparatus according to the third embodiment of the present invention using the calibration apparatus;

DETAILED DESCRIPTION OF THE PREFERRED EMBODIMENTS

Hereinafter, preferred embodiments of an optical measurement apparatus and a calibration apparatus according to the present invention will be described in detail with reference to the drawings. Further, in describing the drawings, the same portions are appended with the same reference signs. Further, the drawings are schematic, and it is to be noted that the relation between the thickness and width of each component and the ratios among the respective components are different from the actual. Further, a portion is included, which has different size relations and ratios among the drawings. The present invention is not limited by the embodiments.

First Embodiment

Figure 1:
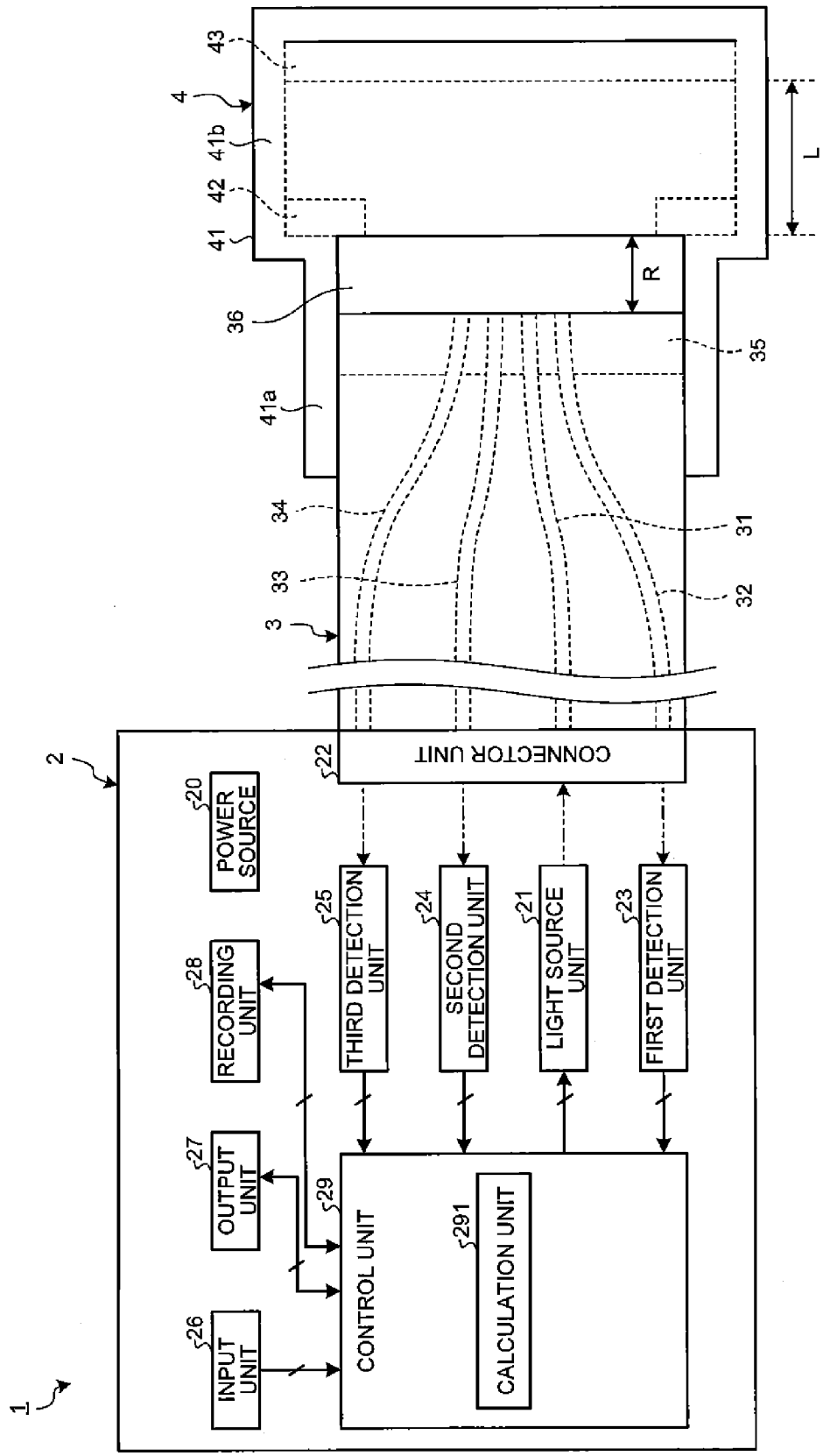
FIG. 1 is a block diagram schematically illustrating a configuration of an optical measurement apparatus and a calibration apparatus according to a first embodiment of the present invention.

FIG. 1 is a block diagram that schematically illustrates a configuration of an optical measurement apparatus and a calibration apparatus according to a first embodiment of the present invention and is a diagram that illustrates a state in which the calibration apparatus has been connected to the optical measurement apparatus.

First, the optical measurement apparatus is described. An optical measurement apparatus 1 illustrated in FIG. 1 includes a main body unit 2 that performs optical measurement with respect to an object to be measured such as body tissue, which is a scattering media, and measures characteristics (properties) of the object to be measured, and a measurement probe 3 that is detachable from the main body unit 2, inserted into a subject.

The main body unit 2 has a power source 20, a light source unit 21, a connector unit 22, a first detection unit 23, a second detection unit 24, a third detection unit 25, an input unit 26, an output unit 27, a recording unit 28, and a control unit 29. The power source 20 supplies electric power to each component of the main body unit 2.

The light source unit 21 irradiates to the measurement probe 3, via the connector unit 22, illumination light to be irradiated onto the object to be measured. The light source unit 21 is realized by using a light source such as a white light emitting diode (LED), a xenon lamp, a tungsten lamp, a halogen lamp, and a laser, and a plurality of lenses. Examples of such lenses include condenser lenses and collimator lenses. The light source unit 21 irradiates illumination light having a wavelength component included in a predetermined wavelength band.

To the connector unit 22, the measurement probe 3 is detachably connected. The connector unit 22 propagates, to the measurement probe 3, the illumination light irradiated by the light source unit 21, and propagates a plurality of light beams entering from the measurement probe 3 respectively to the first detection unit 23, the second detection unit 24, and the third detection unit 25.

The first detection unit 23 detects returned light of the illumination light that has been irradiated from the measurement probe 3 and reflected and/or scattered by the object to be measured, and outputs a result of this detection to the control unit 29. Specifically, the first detection unit 23 detects a spectral component and an intensity distribution of scattered light entering from the measurement probe 3, and outputs a result of this detection to the control unit 29. The first detection unit 23 is realized using a spectrometer, a light receiving sensor, or the like.

The second detection unit 24 is realized by the same configuration as that of the first detection unit 23, detects the returned light of the illumination light that has been irradiated from the measurement probe 3 and reflected and/or scattered by the object to be measured, and outputs a result of this detection to the control unit 29.

The third detection unit 25 is realized by the same configuration as that of the first detection unit 23, detects the returned light of the illumination light that has been irradiated from the measurement probe 3 and reflected and/or scattered by the object to be measured, and outputs a result of this detection to the control unit 29.

The input unit 26 receives and outputs to the control unit 29, input of an instruction signal instructing activation of the main body unit 2, an instruction signal instructing start of measurement of a measurement object S1 by the main body unit 2, an instruction signal instructing a calibration process, and the like. The input unit 26 is realized using a push-type switch, a touch panel, or the like.

The output unit 27 outputs, under control by the control unit 29, various information in the main body unit 2, for example, a result of measurement on the object to be measured. The output unit 27 is realized using a display of a liquid crystal, organic electroluminescence (EL), or the like, and a speaker or the like.

The control unit 29 comprehensively controls the main body unit 2 by carrying out transfer or the like of instruction information or data corresponding to each component of the main body unit 2. The control unit 29 is configured using a central processing unit (CPU) or the like. The control unit 29 has a calculation unit 291.

The calculation unit 291 performs a plurality of calculation processes based on detection results respectively detected by the first detection unit 23, the second detection unit 24, and the third detection unit 25, to calculate characteristic values related to the characteristics of the object to be measured.

Figure 2:
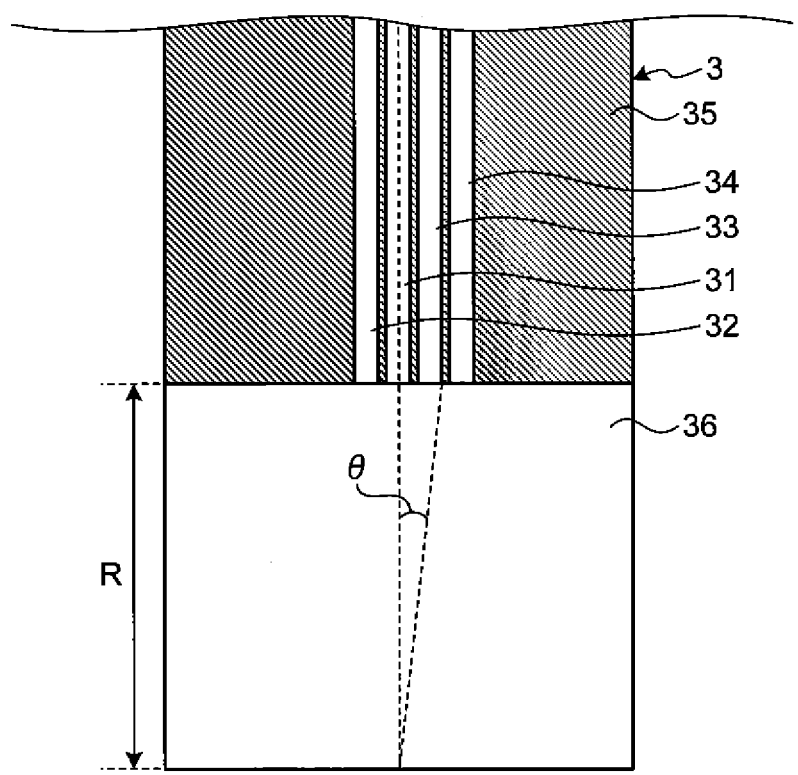
FIG. 2 is a diagram schematically illustrating a cross section of a distal end of a measurement probe of the optical measurement apparatus according to the first embodiment of the present invention, the cross section being cut to include a central axis in a longitudinal direction of the measurement probe.
Figure 3:
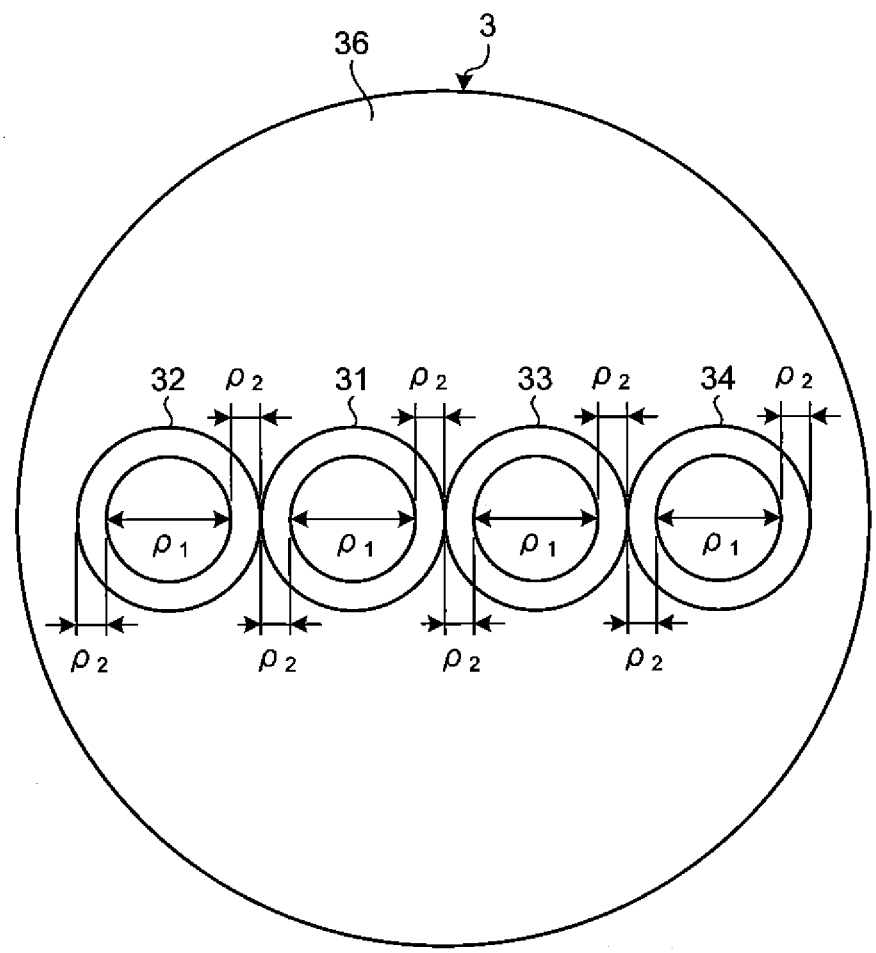
FIG. 3 is a front view of the measurement probe of the optical measurement apparatus according to the first embodiment of the present invention, the front view being viewed from the distal end thereof.

Next, the measurement probe 3 will be described. FIG. 2 is a diagram that schematically illustrates a cross section of the distal end of the measurement probe 3, the cross section being cut to include a central axis in a longitudinal direction of the measurement probe 3. FIG. 3 is a front view of the measurement probe 3 viewed from the distal end thereof.

The measurement probe 3 illustrated in FIGS. 1 to 3 includes an illumination fiber 31, a first detection fiber 32, a second detection fiber 33, a third detection fiber 34, a fiber holding portion 35, and a rod lens (optical element) 36. The illumination fiber 31, the first detection fiber 32, the second detection fiber 33, and the third detection fiber 34 are each realized using an optical fiber having a core diameter of $\rho_1$ and a cladding thickness of $\rho_2$.

The illumination fiber 31 irradiates, via the rod lens 36, the illumination light entering, via the connector unit 22, from the light source unit 21, to the object to be measured or a calibration apparatus 4.

The first detection fiber 32 detects (receives), via the rod lens 36, the returned light of the illumination light that has been irradiated by the illumination fiber 31 and reflected and/or scattered by the object to be measured or the calibration apparatus 4, and propagates the received returned light to the first detection unit 23.

The second detection fiber 33 detects, via the rod lens 36, the returned light of the illumination light that has been irradiated by the illumination fiber 31 and reflected and/or scattered by the object to be measured or the calibration apparatus 4, and propagates the received returned light to the second detection unit 24.

The third detection fiber 34 detects, via the rod lens 36, the returned light of the illumination light that has been irradiated by the illumination fiber 31 and reflected and/or scattered by the object to be measured or the calibration apparatus 4, and propagates the received returned light to the third detection unit 25.

The fiber holding portion 35 holds respective distal ends of the illumination fiber 31, the first detection fiber 32, the second detection fiber 33, and the third detection fiber 34 to be arranged in a straight line or irregularly. Specifically, the fiber holding portion 35 holds the illumination fiber 31, the first detection fiber 32, the second detection fiber 33, and the third detection fiber 34 so that optical axes of the illumination fiber 31, the first detection fiber 32, the second detection fiber 33, and the third detection fiber 34 become parallel to one another. Further, the fiber holding portion 35 fixes the illumination fiber 31, the first detection fiber 32, the second detection fiber 33, and the third detection fiber 34 respectively at predetermined positions so that the returned light of the illumination light enters therein at different angles. For example, the fiber holding portion 35 holds the illumination fiber 31 and the first detection fiber 32 so that a return of the illumination light irradiated from the illumination fiber 31 enters the first detection fiber 32 at an angle $\theta$. The fiber holding portion 35 is realized using a glass, a resin, a metal, or the like.

The rod lens 36 is provided on a distal end of the fiber holding portion 35. The rod lens 36 is realized using a glass, a plastic, or the like having a predetermined transmissivity, and is column-shaped so that distances from the respective distal ends of the illumination fiber 31, the first detection fiber 32, the second detection fiber 33, and the third detection fiber 34 to the object to be measured or to the calibration apparatus 4 become constant.

Next, the calibration apparatus 4 will be described. The calibration apparatus 4 includes a container 41, a stopper portion 42 that prevents insertion of the measurement probe 3, and a reference reflection plate 43 used in a calibration process.

The container 41 is tubular and has an insertion portion 41a through which the measurement probe 3 is insertable, and an accommodation portion 41b that accommodates the reference reflection plate 43. The container 41 is integrally formed of the insertion portion 41a and the accommodation portion 41b.

The stopper portion 42 is ring-shaped and provided in the accommodation portion 41b. The stopper portion 42 prevents the measurement probe 3 from being inserted into the accommodation portion 41b. An inner diameter of the stopper portion 42 is smaller than an outer diameter of the measurement probe 3. The stopper portion 42 keeps a predetermined distance L from an end of the rod lens 36 of the measurement probe 3 to the reference reflection plate 43 constant.

The reference reflection plate 43 is arranged at a position which is away by the predetermined distance L from a distal end portion of the measurement probe 3 in a state in which the measurement probe 3 has been inserted in the insertion portion 41a. The reference reflection plate 43 formed of a material having light reflectivity that is uniform over a wavelength range to be measured in an irradiation plane of the illumination light irradiated by the measurement probe 3. Specifically, a scattering mean free path of a material forming the reference reflection plate 43 is set to be of a larger value than that of a spatial coherence length at the predetermined distance L.

Figure 4:
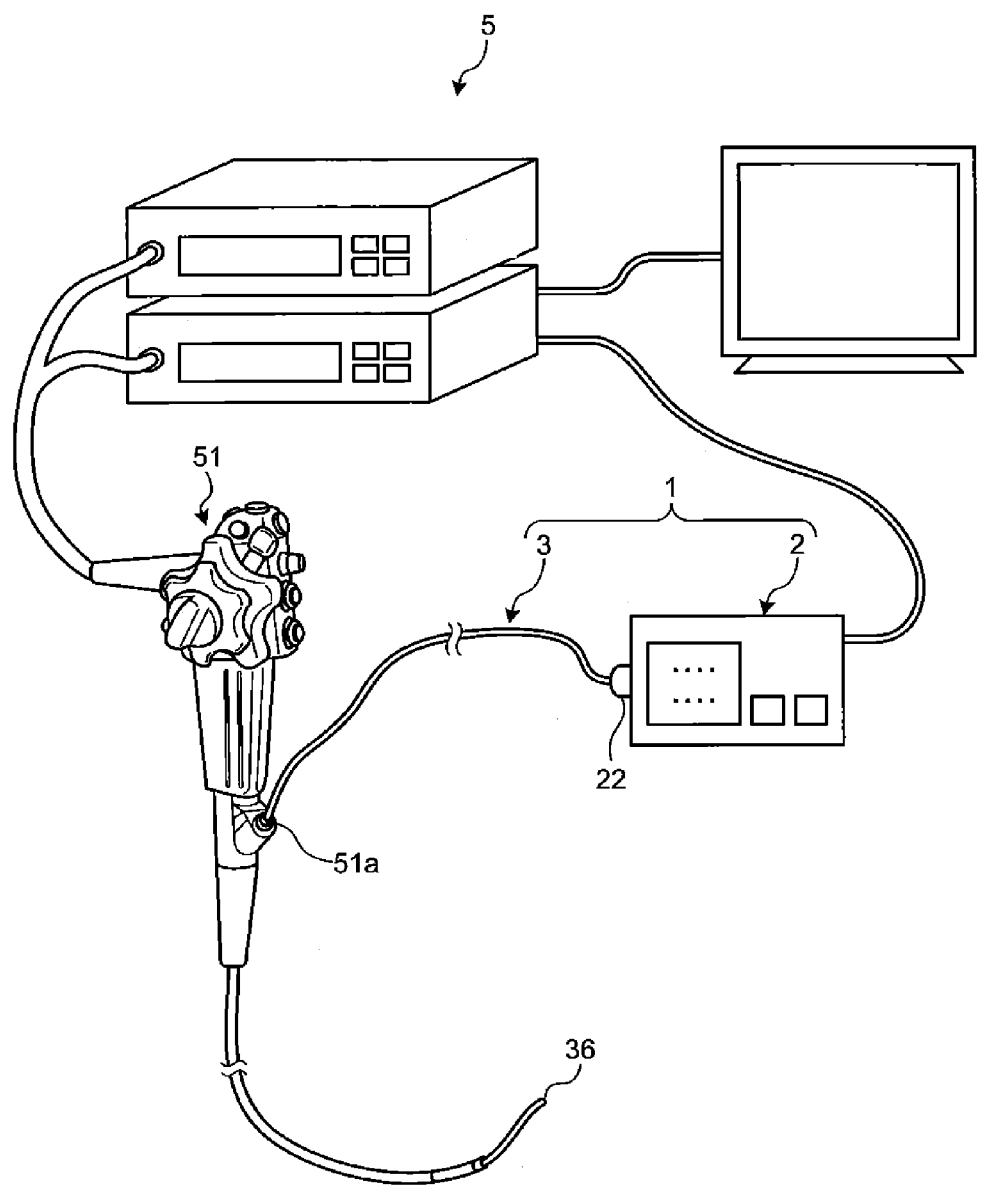
FIG. 4 is a diagram illustrating a situation in which the optical measurement apparatus according to the first embodiment of the present invention is used in an endoscopic system.

In the optical measurement apparatus 1 configured as described above, after a calibration process is performed by the calibration apparatus 4, as illustrated in FIG. 4, the measurement probe 3 is inserted into the subject via a treatment tool channel 51a provided in an endoscopic device 51 (endoscope) of an endoscopic system 5, the illumination fiber 31 irradiates the illumination light to the object to be measured, and the first detection fiber 32, the second detection fiber 33, and the third detection fiber 34 respectively detect, at different scattering angles, the returned light of the illumination light that has been reflected and/or scattered by the object to be measured and propagate the detected returned light to the first detection unit 23, the second detection unit 24, and the third detection unit 25. Thereafter, the calculation unit 291 calculates the characteristic values representing the characteristics of the object to be measured, based on detection results detected respectively by the first detection unit 23, the second detection unit 24, and the third detection unit 25.

Figure 5:
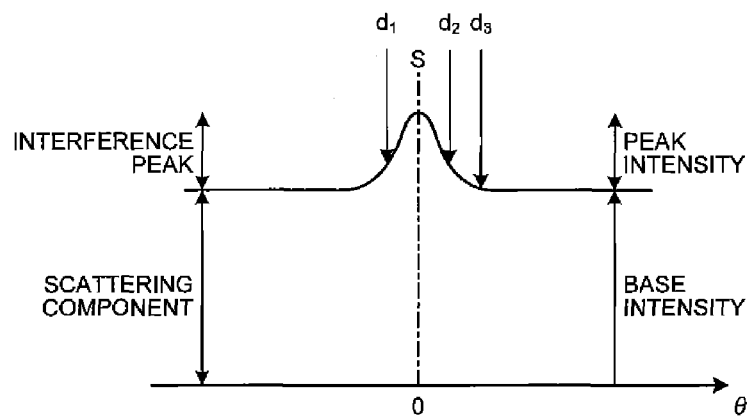
FIG. 5 is a diagram schematically illustrating an interference pattern detected by the optical measurement apparatus according to the first embodiment of the present invention.
Figure 6:
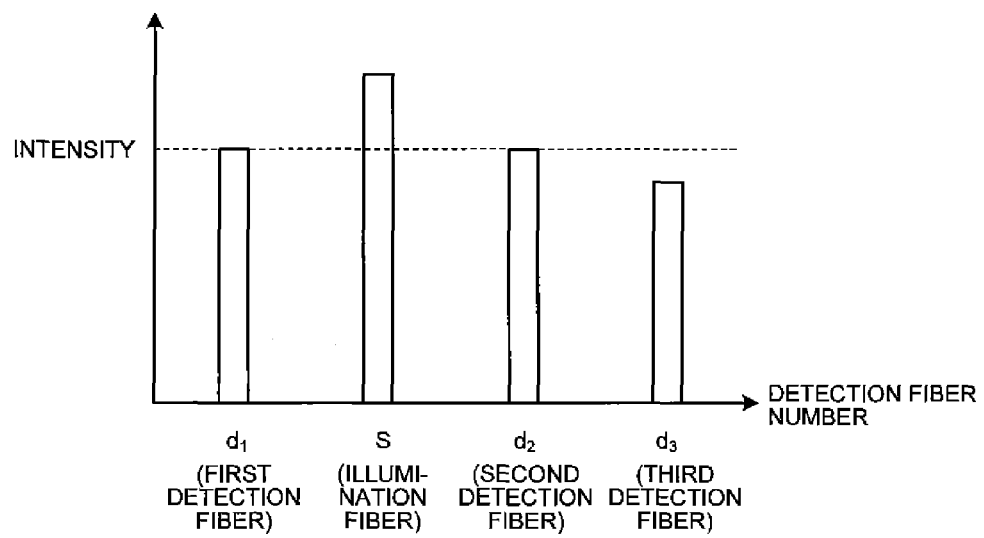
FIG. 6 is a diagram schematically illustrating an intensity of a signal detected by the optical measurement apparatus according to the first embodiment of the present invention.

Next, calibration items of the optical measurement apparatus 1 will be described in detail. FIG. 5 is a diagram that schematically illustrates an interference pattern detected by the optical measurement apparatus 1. FIG. 6 is a diagram that schematically illustrates intensities of signals detected by the optical measurement apparatus 1. In FIGS. 5 and 6, the illumination fiber 31 is described as an illumination fiber S, and the first detection fiber 32, the second detection fiber 33, and the third detection fiber 34 are respectively described as a first detection fiber $d_1$, a second detection fiber $d_2$, and a third detection fiber $d_3$. Further, in FIGS. 5 and 6, the first detection fiber $d_1$ and the second detection fiber $d_2$ correspond to intensities at skirt portions of the interference pattern, and the third detection fiber $d_3$ corresponds to an intensity of a scattered light component of a degree that allows influence of interference to be ignored. Further, in FIG. 6, an intensity detected by a detection fiber S for a case in which the illumination fiber 31 is supposed to be the detection fiber S is also illustrated. In FIG. 6, signal values corresponding to particular wavelengths are illustrated.

Figure 7:
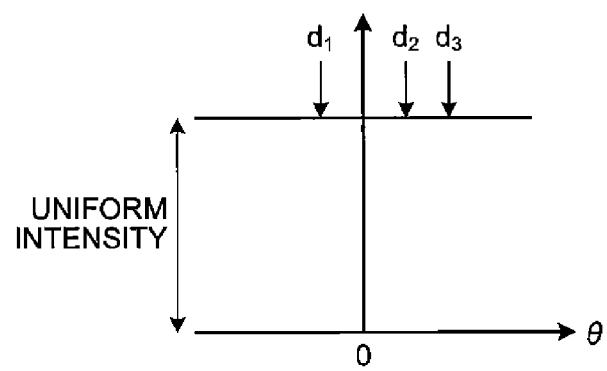
FIG. 7 is a diagram schematically illustrating a signal intensity detected by each detection unit in a signal when light of uniform intensity is irradiated to the measurement probe of the optical measurement apparatus according to the first embodiment of the present invention.
Figure 8:
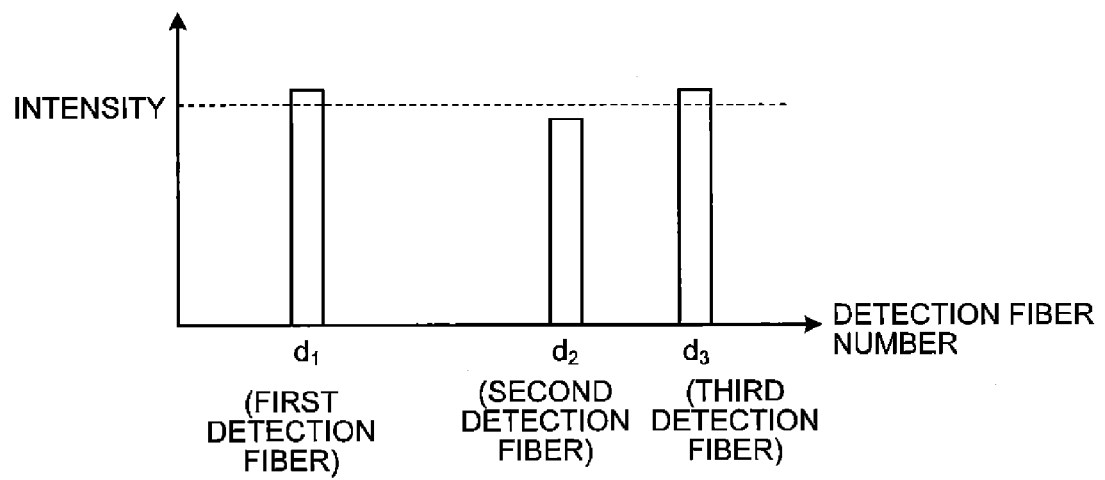
FIG. 8 is a diagram schematically illustrating a signal intensity detected by each detection unit before calibration when light of uniform intensity is irradiated to the measurement probe of the optical measurement apparatus according to the first embodiment of the present invention.
Figure 9:
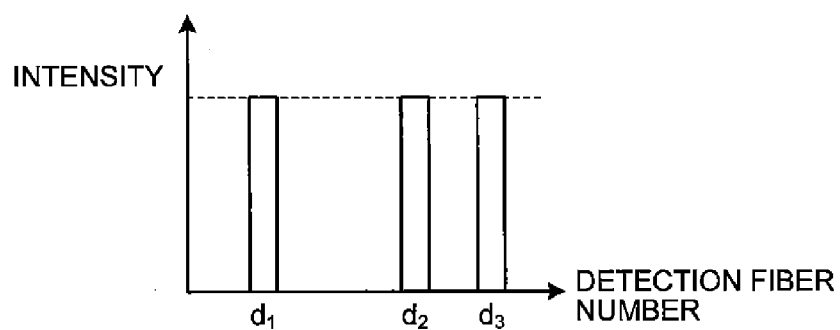
FIG. 9 is a diagram schematically illustrating a signal intensity when a signal intensity detected by each detection unit upon irradiation of light of uniform intensity to the measurement probe of the optical measurement apparatus according to the first embodiment of the present invention is calibrated.

As illustrated in FIGS. 5 and 6, because the signal value detected by the detection fiber S corresponds to the maximum value of the interference pattern, the intensity thereof is the largest. Further, the signal values detected respectively by the first detection fiber $d_1$ and the second detection fiber $d_2$ are of the same intensities, because they are at positions away from the detection fiber S by the same distances. Further, the signal value detected by the third detection fiber $d_3$ is of the smallest intensity. However, the signal values are influenced by variation in light guiding efficiency of detection routes, and variation in detection sensitivity of each of the first detection unit 23, the second detection unit 24, and the third detection unit 25. Accordingly, as illustrated in FIG. 7, even if light of uniform intensity is irradiated to the measurement probe 3, the signal values detected respectively by the first detection fiber $d_1$, the second detection fiber $d_2$, and the third detection fiber $d_3$ do not become constant (see FIG. 8). Therefore, as illustrated in FIG. 9, calibration to make detection intensities respectively detected by the first detection fiber $d_1$, the second detection fiber $d_2$, and the third detection fiber $d_3$ constant is needed.

Figure 10:
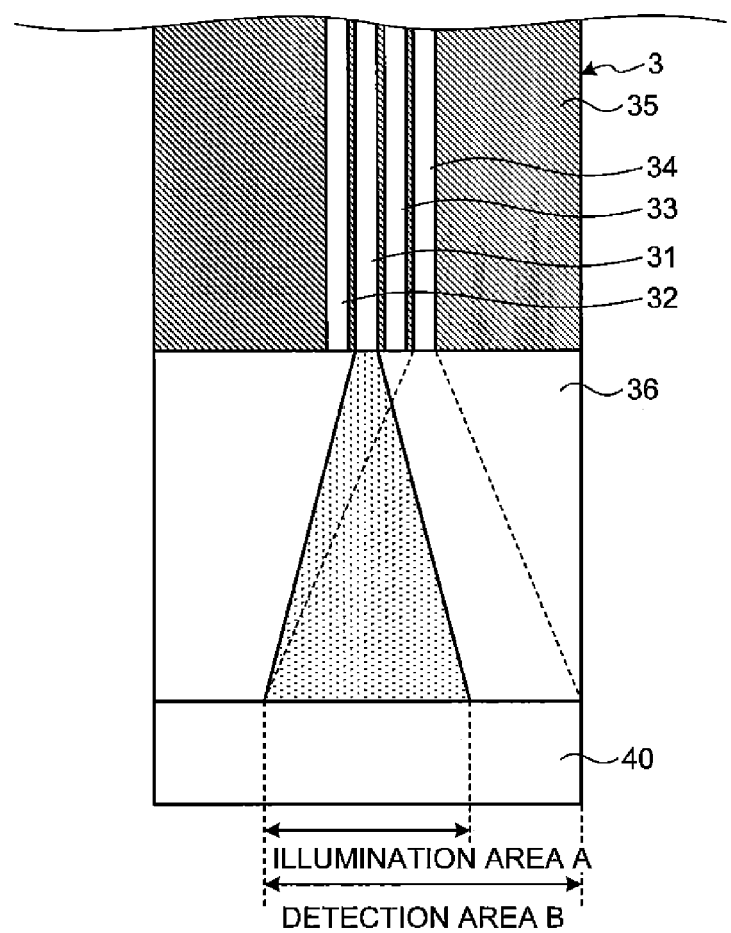
FIG. 10 is a diagram schematically illustrating an illumination area to which the measurement probe of the optical measurement apparatus according to the first embodiment of the present invention is irradiated and a detection area over which returned light of the illumination light is detected.

Further, as illustrated in FIG. 10, an illumination area A to which the illumination fiber 31 irradiates the illumination light does not coincide with a detection area B for which the first detection fiber 32, the second detection fiber 33, and the third detection fiber 34 each detect the returned light of the illumination light, and thus variation in the signal values is generated. For example, as illustrated in FIG. 10, the illumination area A to which the illumination fiber 31 irradiates the illumination light and the detection area B over which the third detection fiber 34 detects the returned light of the illumination light are different from each other. Therefore, the optical measurement apparatus 1 needs to perform correction of detection signals according to variation in a detection range of the object to be measured.

Next, the reference reflection plate 43 of the calibration apparatus 4 will be described in detail. In the calibration apparatus 4, for the above mentioned calibration items, material properties of the reference reflection plate 43 are set, correspondingly with a degree of spatial coherence on the reference reflection plate 43, i.e., a spatial coherence length Lsc, to satisfy Condition (1) or Condition (2).

$$ls^* \geq 2Lsc, \text{ AND } g \leq 0.85 \quad (1):$$

$$ls^* \approx 2Lsc, \text{ AND } g > 0.85 \quad (2):$$

Herein, ls* represents the scattering mean free path of the material forming the reference reflection plate 43, and "g" represents an anisotropic parameter in a scattering direction of the reference reflection plate 43. For Condition (2), a range of ls*/Lsc=1 to 3 is only needed.

Further, as illustrated in FIG. 1, when a length in a fiber longitudinal direction of the rod lens 36 is "R", a distance from the distal end of the measurement probe 3 to the reference reflection plate 43 is "L", a refractive index of the rod lens 36 at a prescribed wavelength λ is "n", and a core diameter of the illumination fiber 31 is $\rho_1$, the spatial coherence length Lsc at a detection position of the reference reflection plate 43 is defined by Equation (3) below.

$$Lsc = \lambda(R/n+L)/\pi\rho_1 \quad (3)$$

As described above, in the calibration apparatus 4, based on Condition (1) or Condition (2): the scattering mean free path ls* of the reference reflection plate 43 is preset and the distance L is set such that the spatial coherence length Lsc satisfies Condition (1) or Condition (2); or the distance L of the reference reflection plate 43 is preset and the material of the reference reflection plate 43 is adjusted or selected such that the scattering mean free path ls* satisfies Condition (1) or Condition (2). In this case, because for the reference reflection plate 43, a material having reflectivity that is constant regardless of wavelength needs to be selected, preferably, the scattering mean free path ls* of the reference reflection plate 43 is set, and the distance L is set such that the spatial coherence length Lsc satisfies Condition (1) or Condition (2). Even if a value of the scattering mean free path ls* of the material forming the reference reflection plate 43 is not accurately known, intensity change detected by any of the first detection fiber 32, the second detection fiber 33, and the third detection fiber 34 may be detected by changing a position of the reference reflection plate 43 and the distance L may be set to a position at which the detection intensities of the first detection fiber 32 and the second detection fiber 33 are of the minimum values.

Condition (1) and Condition (2) will now be described in detail. According to Condition (1) and Condition (2), a shape of the interference pattern, which is formed at the distal end of the measurement probe 3 when the illumination light from the measurement probe 3 is reflected and/or scattered and becomes the returned light, is determined by the spatial coherence length Lsc at a position of the reference reflection plate 43 and the scattering mean free path ls* of the reference reflection plate 43 (see Non-Patent Literature 2).

Figure 11:
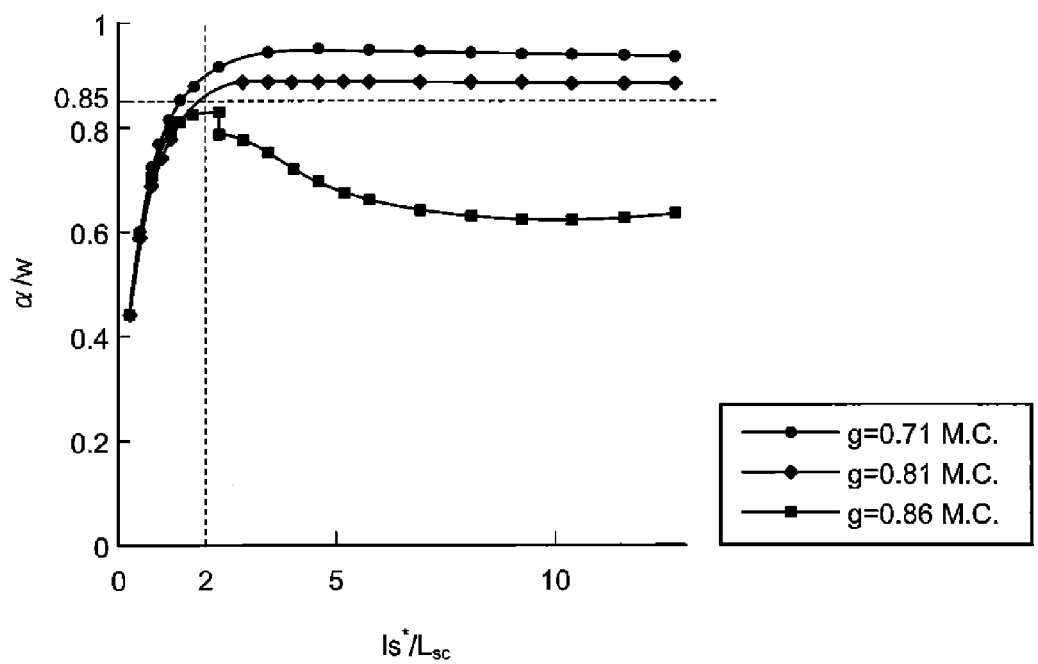
FIG. 11 is a diagram illustrating a relation between a value of a ratio of a scattering mean free path to a spatial coherence length and a value of a ratio obtained by dividing an apparent light source size by a full width at half maximum of an interference pattern.
Figure 12:
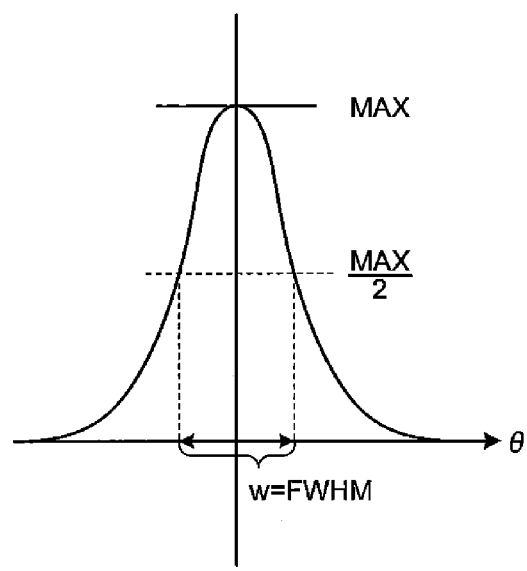
FIG. 12 is a diagram schematically illustrating a full width at half maximum of an interference pattern.

FIG. 11 is a diagram that illustrates a relation between a value of a ratio of the scattering mean free path ls* to the spatial coherence length Lsc and a value of a ratio obtained by dividing an apparent light source size by a full width at half maximum (FWHM) w of the interference pattern. FIG. 12 is a diagram that schematically illustrates the full width at half maximum w.

As illustrated in FIG. 11, when the anisotropic parameter g in the scattering direction of the reference reflection plate 43 is less than 0.85, a value of α/w tends to converge from around where a value of ls*/Lsc becomes greater than 2. Further, when the anisotropic parameter g in the scattering direction of the reference reflection plate 43 is greater than 0.85, the value α/w becomes maximum around where the value of ls*/Lsc is 2. Therefore, when the value becomes maximum around where the value of ls*/Lsc is 2, the full width at half maximum w of the interference pattern becomes the smallest.

As described above, under the condition where the full width at half maximum w of the interference pattern becomes the smallest, the interference pattern does not enter the first detection fiber 32 to the third detection fiber 34 and at a position of the detection fiber, a luminous flux of uniform intensity is obtained. Accordingly, from a relation between the full width at half maximum w and scattering properties of a scattering medium (ls*/Lsc and g) illustrated in FIG. 11, Condition (1) and Condition (2) are able to be derived as conditions under which the full width at half maximum w becomes the smallest.

Figure 13:
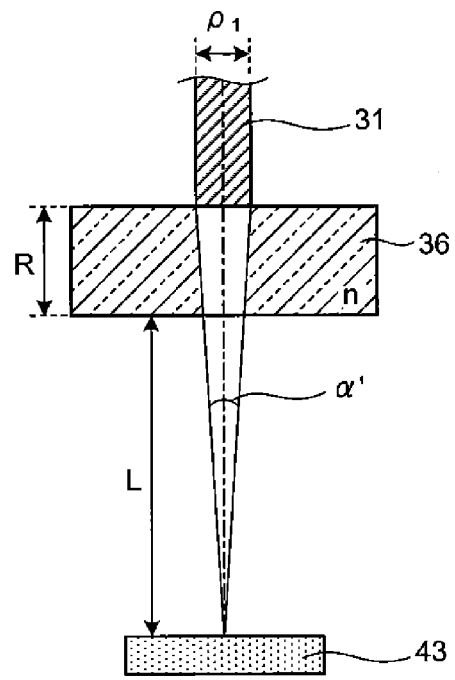
FIG. 13 is a diagram schematically illustrating a quantity represented by a ratio of a core diameter of an illumination fiber to a distance to a reference reflection plate.

Further, the apparent light source size a illustrated in FIGS. 11 and 12, is, as illustrated in FIG. 13, a quantity represented by Equation (4) below where a numerator is the core diameter $\rho_1$ of the illumination fiber 31 and a denominator is a sum of the distance L from the illumination fiber 31 to the reference reflection plate 43 and a value R/n obtained by dividing the length R of the rod lens 36 by the refractive index n of the rod lens 36.

$$\alpha = \rho_1/(R/n+L) \quad (4)$$

When α of Equation (4) is small (α<0.1), α becomes equal to an angle α' [rad] illustrated in FIG. 13. Therefore, the vertical axis α/w of FIG. 11 can be said to be an index indicating the extent to which the full width at half maximum w of the interference pattern fits in an angle range a corresponding to the core $\rho_1$ of the illumination fiber 31.

Figure 14:
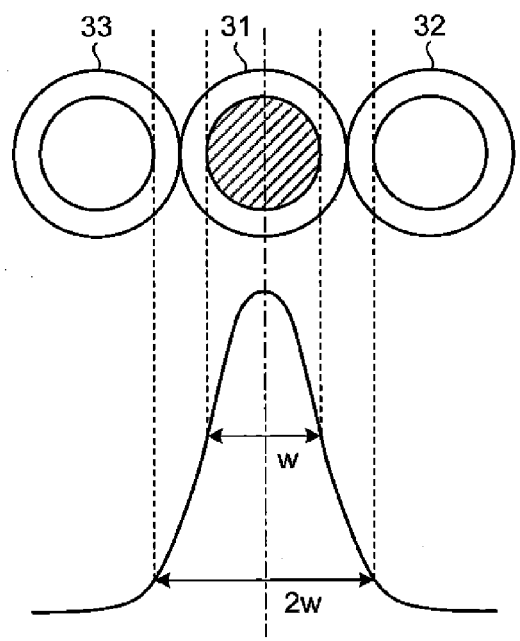
FIG. 14 is a diagram corresponding to a case in which an interference peak corresponding to a full width at half maximum of an interference pattern fits within a core of the illumination fiber.

FIG. 14 is a diagram when α/w=1, and an interference peak corresponding to the full width at half maximum w of the interference pattern fits in the core $\rho_1$ of the illumination fiber 31.

As illustrated in FIG. 14, the optical measurement apparatus 1 considers a condition under which skirt of the interference pattern is not in the respective cores of the first detection fiber 32 and the second detection fiber 33. Under this condition, the core of the detection fiber 32 is positioned outer than about a position corresponding to twice (2w) the full width at half maximum w. Specifically, it is important that the skirt of the interference pattern is not in the respective cores of the first detection fiber 32 and the second detection fiber 33. In FIG. 14, a case in which α/w=1 is illustrated, but the full width at half maximum w is not necessarily in the core $\rho_1$ of the illumination fiber 31. For example, if α/w=1 is not true, the full width at half maximum w just needs to be not in the respective cores of the first detection fiber 32 and the second detection fiber 33. Such a situation would be a case in which the thicknesses of the claddings of the first detection fiber 32 to the third detection fiber 34 and the illumination fiber 31 are thick.

Further, as illustrated in FIG. 3, when the core diameter of the illumination fiber 31 is $\rho_1$ and the thickness of the cladding thereof (hereinafter, "cladding thickness") is $\rho_2$, the full width at half maximum w satisfies Condition (5) below.

$$(\rho_1+4\rho_2)/(R/n+L)>2w \quad (5):$$

Figure 15:
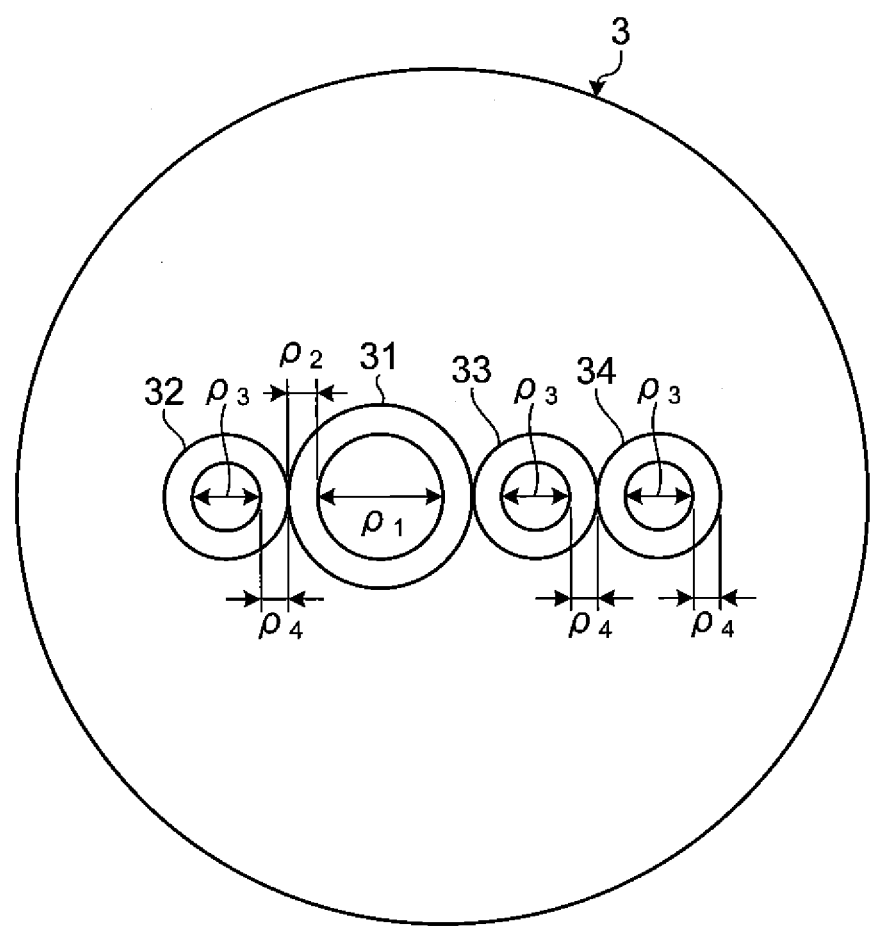
FIG. 15 is a diagram illustrating a case in which core diameters and cladding thicknesses differ between an illumination fiber and detection fibers.

As illustrated in FIG. 15, when the core diameter of the illumination fiber 31 is $\rho_1$, the cladding thickness thereof is $\rho_2$, the respective core diameters of the first detection fiber 32, the second detection fiber 33, and the third detection fiber 34 are $\rho_3$, and the cladding thicknesses thereof are $\rho_4$, the full width at half maximum w satisfies Condition (6) below.

$$(\rho_1+2\rho_2+2\rho_4)/(R/n+L)>2w \quad (6):$$

As described above, in the measurement probe 3, because a light guiding property of each fiber is maintained and thus the cladding thicknesses are set to be thick, the above Condition (5) or Condition (6) is satisfied.

Figure 16:
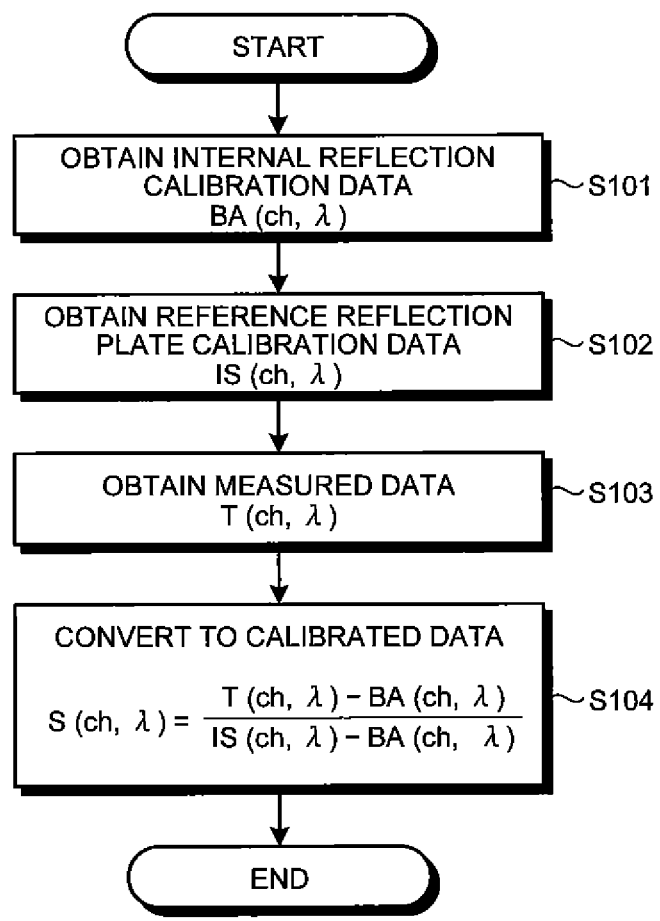
FIG. 16 is a flow chart illustrating an outline of a calculation process including a calibration process executed by the optical measurement apparatus according to the first embodiment of the present invention.

Next, a calculation process including the calibration process performed by the optical measurement apparatus 1 is described. FIG. 16 is a flow chart that illustrates an outline of the calculation process including the calibration process performed by the optical measurement apparatus 1. Hereinafter, "ch" represents each detection fiber number and λ represents wavelength.

Figure 17:
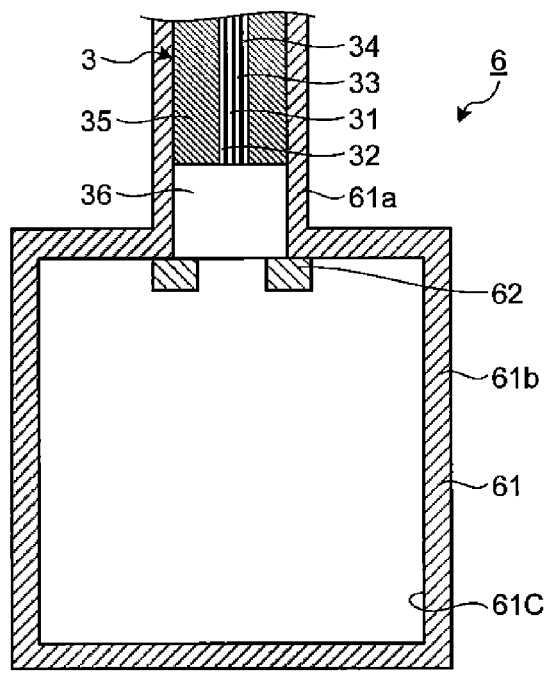
FIG. 17 is a diagram schematically illustrating a cross section of an absorbing apparatus according to the first embodiment of the present invention.

As illustrated in FIG. 16, the optical measurement apparatus 1 obtains internal reflection calibration data BA (ch, λ) by inserting absorbing apparatus as illustrated in FIG. 17. (Step S101). FIG. 17 is a diagram that schematically illustrates a cross section of an absorbing apparatus according to the first embodiment of the present invention. A absorbing apparatus 6 illustrated in FIG. 17 includes a container 61 that is approximately a cuboid and a stopper portion 62 that prevents insertion of the measurement probe 3.

The stopper portion 62 is ring-shaped and provided in the accommodation portion 61b. The stopper portion 62 prevents the measurement probe 3 from being inserted into the accommodation portion 61b. An inner diameter of the stopper portion 62 is smaller than an outer diameter of the measurement probe 3. The stopper portion 62 keeps a distance L from the end of the rod lens 36 of the measurement probe 3 to a bottom surface of the accommodation portion 61b constant.

The container 61 has an insertion portion 61a into which the measurement probe 3 is insertable, and an accommodation portion 61b having an inner surface formed of a light absorption portion 61c provided with a member that does not reflect light or a light absorption member that absorbs wavelength of light irradiated by the light source unit 21. Specifically, the light absorption portion c1c is coated in black. Specifically, the optical measurement apparatus 1 obtains, by irradiating, in the insertion portion 61a of the calibration apparatus 6, the illumination light to the illumination fiber 31, internal reflection calibration data in a measurement probe detected by the first detection unit 23, the second detection unit 24, and the third detection unit 25.

Subsequently, the optical measurement apparatus 1 obtains, in a state in which the distal end of the measurement probe 3 has come into contact with the stopper portion 42, reference reflection plate calibration data IS (ch, λ) of the reference reflection plate 43 (Step S102). Specifically, the optical measurement apparatus 1, obtains, by the illumination fiber 31 irradiating the illumination light to the reference reflection plate 43 in a state in which the distal end of the rod lens 36 of the measurement probe 3 has come into contact with the stopper portion 42, reference reflection plate calibration data of the reference reflection plate 43, the reference reflection plate calibration data having been detected by each of the first detection unit 23, the second detection unit 24, and the third detection unit 25.

Thereafter, the optical measurement apparatus 1 obtains measured data T (ch, λ) of the object to be measured (Step S103). Specifically, the optical measurement apparatus 1 obtains, by the illumination fiber 31 irradiating the illumination light to the object to be measured, measured data detected by each of the first detection unit 23, the second detection unit 24, and the third detection unit 25.

Subsequently, the calculation unit 291 converts, using the internal reflection calibration data BA (ch, λ) and the reference reflection plate calibration data IS (ch, λ), the measured data T (ch, λ) into calibrated data S (ch, λ) (Step S104). Specifically, the calculation unit 291 converts the measured data T (ch, λ) into the calibrated data S (ch, λ) by Equation (7) below.

$$S(ch,\lambda)=(T(ch,\lambda)-BA(ch,\lambda))/(IS(ch,\lambda)-BA(ch,\lambda)) \qquad (7)$$

According to the above described first embodiment of the present invention, the reference reflection plate 43 is included, which is arranged at the position away by the predetermined distance L from the distal end portion of the measurement probe 3 in the state in which the measurement probe 3 has been inserted in the insertion portion 41a, and for the reference reflection plate 43, the scattering mean free path of the material forming the reference reflection plate 43 is set to be larger than the spatial coherence length Lsc determined using the predetermined distance L. As a result, complicated plural calibration items are readily obtainable in one operation.

Second Embodiment

Next, a second embodiment of the present invention will be described. In the second embodiment, a configuration of a calibration apparatus is different from the calibration apparatus according to the above described first embodiment. Therefore, hereinafter, the configuration of the calibration apparatus according to the second embodiment will be described. Configurations that are the same as those of the optical measurement apparatus 1 and the calibration apparatus 4 according to the above described first embodiment will be described being appended by the same reference signs.

Figure 18:
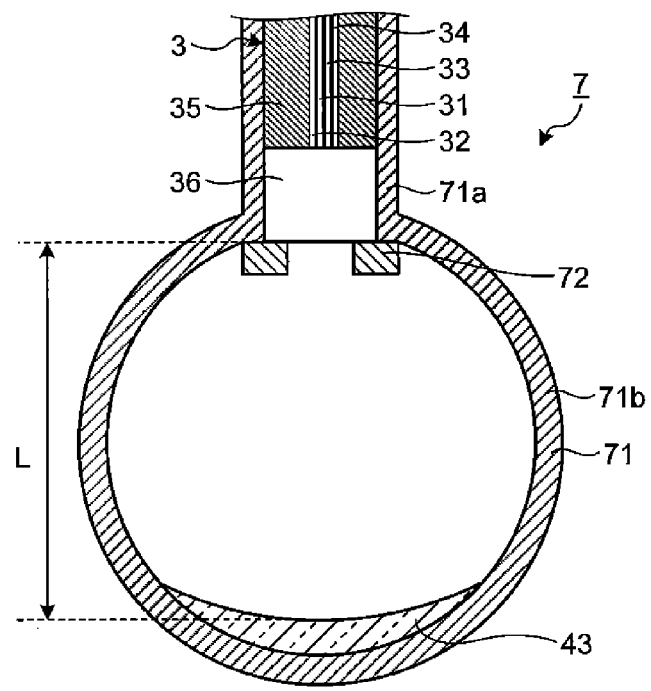
FIG. 18 is a diagram schematically illustrating a cross section of a calibration apparatus according to a second embodiment of the present invention.

In the second embodiment, a spherical formation may be employed. FIG. 18 is a diagram that schematically illustrates a cross section of a calibration apparatus according to a second embodiment. A calibration apparatus 7 illustrated in FIG. 18 includes a container 71 that is approximately spherical and a stopper portion 72 that prevents insertion of the measurement probe 3.

The container 71 has an insertion portion 71a into which the measurement probe 3 is insertable, and an accommodation portion 71b that accommodates the reference reflection plate 43.

Third Embodiment

Next, a third embodiment of the present invention will be described. The third embodiment has a different configuration for a calibration apparatus. Therefore, hereinafter, the configuration of the calibration apparatus according to the third embodiment will be described. Configurations that are the same as those of the optical measurement apparatus 1 and the calibration apparatus 4 according to the above described first embodiment will be described being appended by the same reference signs.

Figure 19:
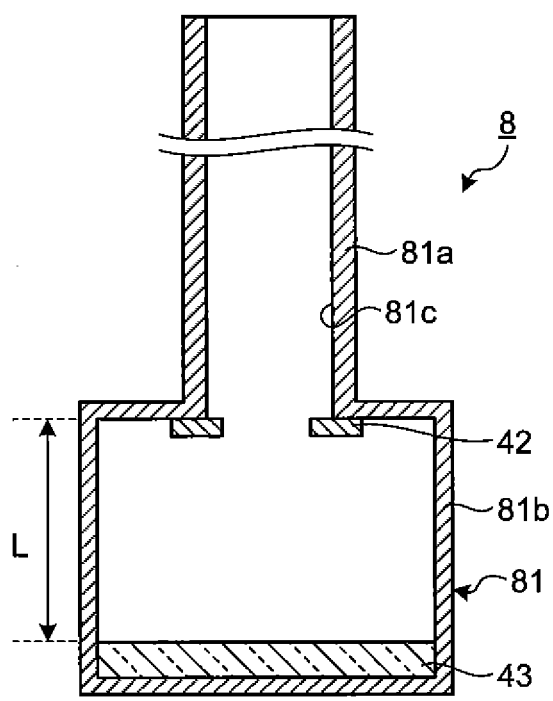
FIG. 19 is a diagram schematically illustrating a cross section of a calibration apparatus according to a third embodiment of the present invention.

FIG. 19 is a diagram that schematically illustrates a cross section of the calibration apparatus according to the third embodiment. A calibration apparatus 8 illustrated in FIG. 19 includes a container 81, a stopper portion 42, and the reference reflection plate 43.

The container 81 has an insertion portion 81a through which the measurement probe 3 is insertable, and an accommodation portion 81b that accommodates the reference reflection plate 43, and the container 81 is formed integrally of the insertion portion 81a and the accommodation portion 81b.

The insertion portion 81a has, on an inner surface thereof, a light absorption portion 81c provided with a member that does not reflect light or a light absorption member that absorbs wavelength of light irradiated by the light source unit 21. Specifically, the light absorption portion 81c is coated in black.

A calibration process performed using the calibration apparatus 8 configured as above will be described. FIG. 20 is a diagram that schematically illustrates an outline of the calibration process, which the optical measurement apparatus 1 performs, using the calibration apparatus 8.

As illustrated in FIG. 20, the optical measurement apparatus 1 obtains, when the illumination fiber 31 irradiates the illumination light to the light absorption portion 81c in the insertion portion 81a, internal reflection calibration data detected by each of the first detection unit 23, the second detection unit 24, and the third detection unit 25 (FIG. 20(a) to FIG. 20(b)). In this case, the optical measurement apparatus 1 may obtain the internal reflection calibration data when a user stops the insertion of the measurement probe 3 midway through the insertion portion 81a. Further, the calculation unit 291 may continuously obtain the internal reflection calibration data until the measurement probe 3 comes into contact with the stopper portion 42 and select, as an internal reflection calibration data to be used in the calibration process, data indicating the minimum intensity, from the obtained internal reflection calibration data. This step is corresponds to the step S101 in FIG. 16.

Subsequently, the optical measurement apparatus 1 obtains the reference reflection plate calibration data detected by the first detection unit 23, the second detection unit 24, and the third detection unit 25 when the illumination fiber 31 irradiates the illumination light to the reference reflection plate 43 (FIG. 20(b)). Preferably, the calculation unit 291 selects, as the reference reflection plate calibration data, data indicating the maximum intensity detected by the first detection unit 23, the second detection unit 24, and the third detection unit 25 when the distal end of the measurement probe 3 comes into contact with the stopper portion 42. This step is corresponds to the step S102 in FIG. 16.

According to the above described third embodiment of the present invention, just by a single operation of inserting the measurement probe 3 into the insertion portion 81a of the calibration apparatus 8, plural calibration items are able to be performed simultaneously. As a result, complicated operations are able to be lessened, and damage to the measurement probe 3 during calibration processes and forgetting to take calibration data are preventable.

Further, according to the third embodiment, plural calibration items are able to be performed simultaneously with a simple configuration.

In the third embodiment of the present invention, a position of the reference reflection plate 43 may be movably provided by a drive unit such as a motor, and while adjusting the distance from the measurement probe 3 to the reference reflection plate 43, the optical measurement apparatus 1 may measure the reference reflection plate calibration data and the internal reflection calibration data.

Fourth Embodiment

Next, a fourth embodiment of the present invention will be described. The fourth embodiment has a different configuration for a calibration apparatus. Therefore, hereinafter, the configuration of the calibration apparatus according to the fourth embodiment will be described. Configurations that are the same as those of the optical measurement apparatus 1 and the calibration apparatus 4 according to the above described first embodiment will be described being appended by the same reference signs.

Figure 21:
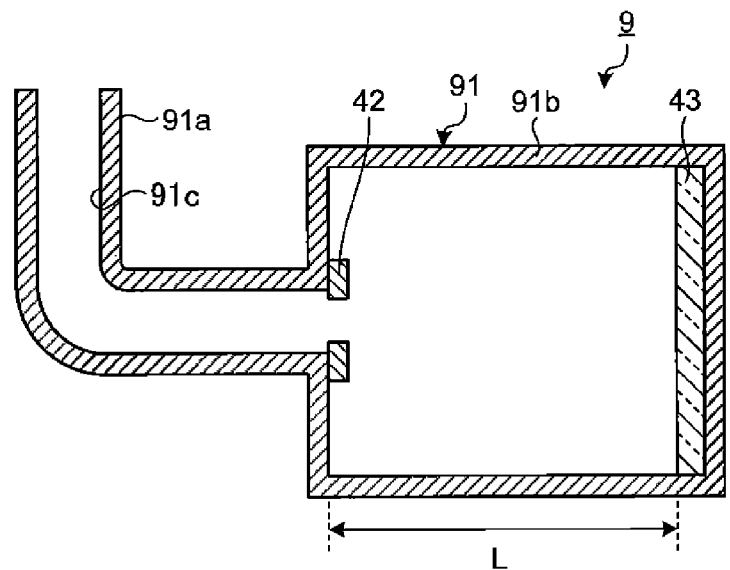
FIG. 21 is a diagram schematically illustrating a cross section of a calibration apparatus according to a fourth embodiment of the present invention.

FIG. 21 is a diagram that schematically illustrates a cross section of the calibration apparatus according to the fourth embodiment. A calibration apparatus 9 illustrated in FIG. 21 includes a container 91, the stopper portion 42, and the reference reflection plate 43.

The container 91 has an insertion portion 91a through which the measurement probe 3 is inserted, and an accommodation portion 91b that accommodates the reference reflection plate 43. The container 91 is integrally formed of the insertion portion 91a and the accommodation portion 91b. The insertion portion 91a is tubular and connected to the accommodation portion 91b with a portion of the insertion portion 91a being bent.

When a calibration process is performed using the calibration apparatus 9 configured as above, the optical measurement apparatus 1 obtains internal reflection correction data before the bend of the insertion portion 91a. When this is done, the illumination light irradiated from the measurement probe 3 will not be irradiated to the reference reflection plate 43 and thus the returned light of the illumination light is preventable from influencing the measurement probe 3.

According to the above described fourth embodiment of the present invention, because the portion of the insertion portion 91a is bent, upon the calibration of the internal reflection correction, the influence by the returned light from the reference reflection plate 43 is preventable and thus an accurate calibration process is able to be performed.

According to the fourth embodiment, an angle of the bend of the insertion portion 91a is approximately 90 degrees, but the insertion portion 91a only needs to be bent to an extent such that the reference reflection plate 43 is not visible at the front of the measurement probe 3 and the angle of the bend may be changed as appropriate in order to ensure operability.

In the fourth embodiment of the present invention, the position of the reference reflection plate 43 may be movably provided by a drive unit such as a motor, and while adjusting the distance from the measurement probe 3 to the reference reflection plate 43, the optical measurement apparatus 1 may measure the reference reflection plate calibration data and the internal reflection calibration data.

Fifth Embodiment

Next, a fifth embodiment of the present invention will be described. The fifth embodiment has a different configuration for a calibration apparatus. Therefore, hereinafter, the configuration of the calibration apparatus according to the fifth embodiment will be described. Configurations that are the same as those of the optical measurement apparatus 1 and the calibration apparatus 4 according to the above described first embodiment will be described being appended by the same reference signs.

Figure 22:
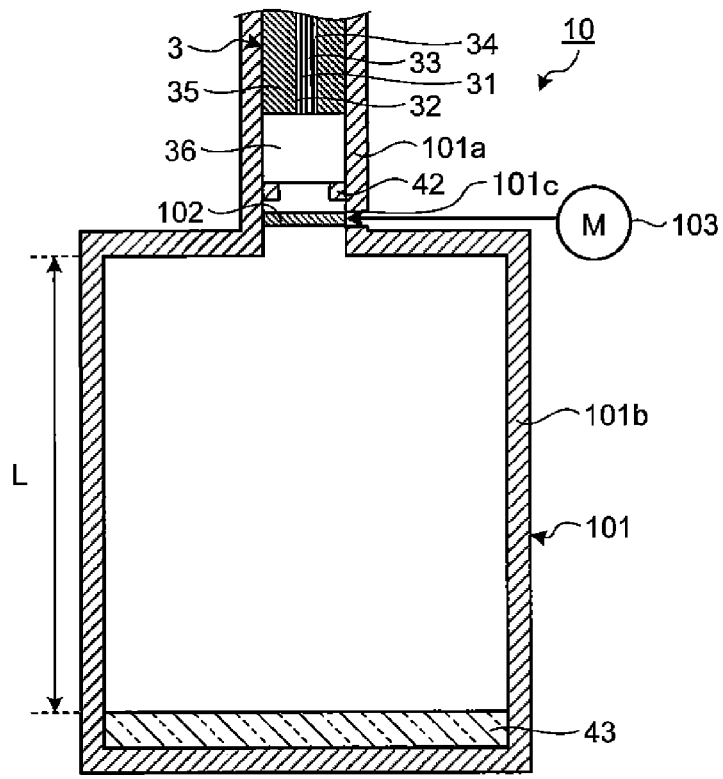
FIG. 22 is a diagram schematically illustrating a cross section of a calibration apparatus according to a fifth embodiment of the present invention.
Figure 23:
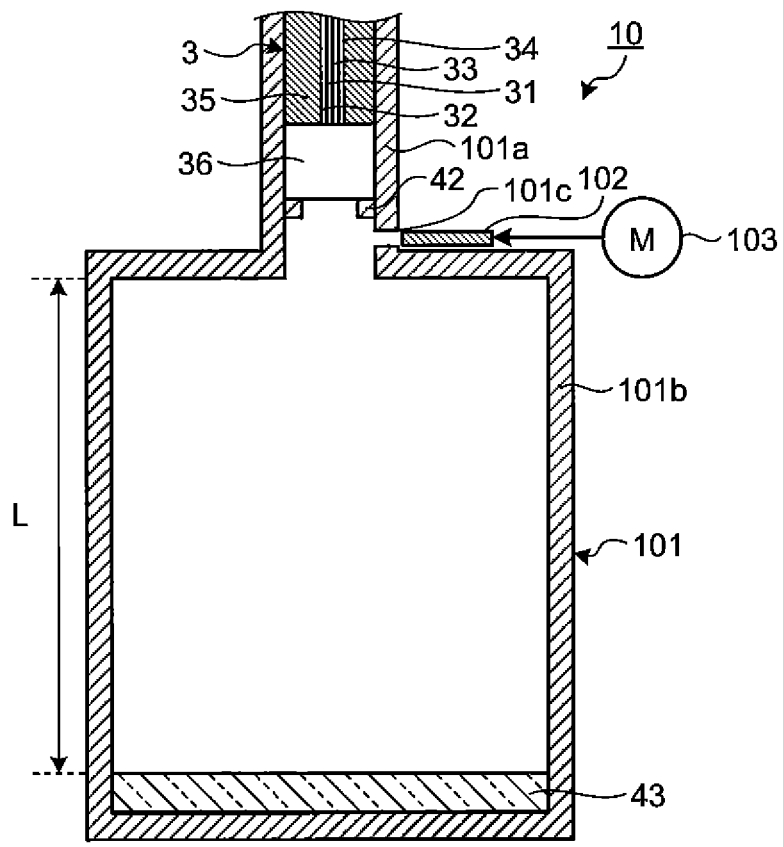
FIG. 23 is a diagram schematically illustrating the cross section of the calibration apparatus according to the fifth embodiment of the present invention.

FIGS. 22 and 23 are diagrams that each schematically illustrates a cross section of the calibration apparatus according to the fifth embodiment. A calibration apparatus 10 illustrated in FIGS. 22 and 23 includes a container 101, the stopper portion 42, the reference reflection plate 43, a shutter 102, and a drive unit 103.

The container 101 has an insertion portion 101a through which the measurement probe 3 is inserted, and an accommodation portion 101b that accommodates the reference reflection plate 43. The container 101 is integrally formed of the insertion portion 101a and the accommodation portion 101b. Further, the insertion portion 101a has a hole 101c provided therein, through which the shutter 102 is retractably insertable. Further, the insertion portion 101a has the stopper portion 42 provided therein.

The shutter 102 is circular and shields the illumination light irradiated by the measurement probe 3. The shutter 102 is formed using a black plate, which uses a light absorption member or the like.

The drive unit 103 retractably drives the shutter 102 with respect to the hole 101c. The drive unit 103 is configured using a DC motor, a stepping motor, or the like.

A calibration process performed by the optical measurement apparatus 1 using the calibration apparatus configured as above will be described. The optical measurement apparatus 1 obtains the internal reflection calibration data. In this case, as illustrated in FIG. 22, the shutter 102 is arranged on an optical axis of the illumination light irradiated by the measurement probe 3, and shields the illumination light irradiated by the measurement probe 3.

Subsequently, by driving the drive unit 103, the calibration apparatus 10 retracts the shutter 102 from the hole 101c of the insertion portion 101a (see FIG. 23).

Thereafter, the optical measurement apparatus 1 obtains the reference reflection plate calibration data by irradiating the illumination light to the reference reflection plate 43.

According to the above described fifth embodiment of the present invention, calibration items of the optical measurement apparatus 1 are automatically changeable, and thus plural calibration items are able to be readily performed in one operation.

Sixth Embodiment

Next, a sixth embodiment of the present invention will be described. The sixth embodiment has a different configuration for a calibration apparatus. Therefore, hereinafter, the configuration of the calibration apparatus according to the sixth embodiment will be described. Configurations that are the same as those of the optical measurement apparatus 1 and the calibration apparatus 4 according to the above described first embodiment will be described being appended by the same reference signs.

Figure 24:
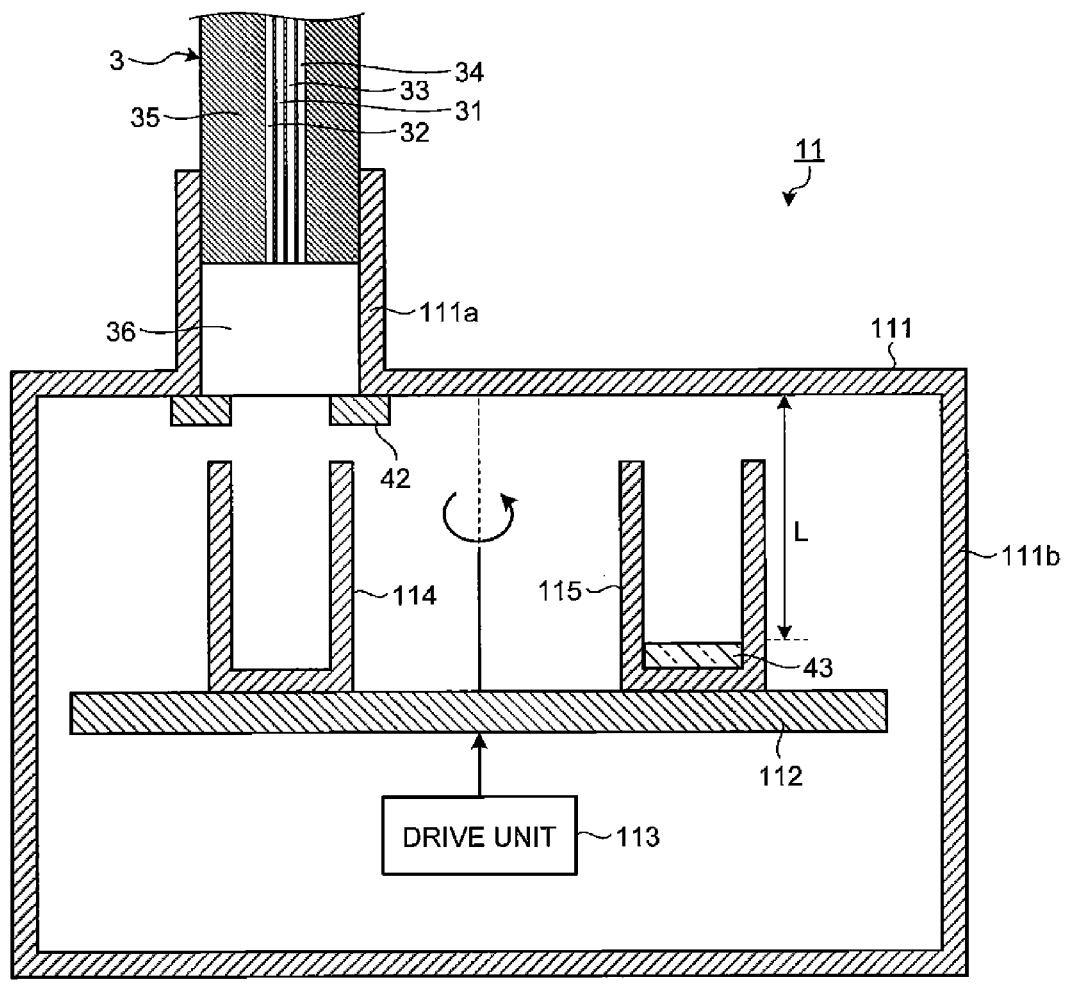
FIG. 24 is a diagram schematically illustrating a cross section of a calibration apparatus according to a sixth embodiment of the present invention.

FIG. 24 is a diagram that schematically illustrates a cross section of the calibration apparatus according to the sixth embodiment. A calibration apparatus 11 illustrated in FIG. 24 includes: an accommodation unit 111b, which has a space inside, and into which the measurement probe 3 is inserted through an insertion portion 111a; the stopper portion 42, which is provided in the accommodation unit 111b and prevents insertion of the measurement probe 3; a rotation plate 112, which rotates about a predetermined axis; a drive unit 113, which causes the rotation plate 112 to rotate; a first container 114, which has an inner surface provided with a light absorption member and used when the internal reflection calibration data are obtained; and a second container 115, which accommodates the reference reflection plate 43 that is away from the stopper portion 42 by a distance L.

A calibration process performed by the optical measurement apparatus 1 using the calibration apparatus 11 configured as above will be described. The optical measurement apparatus 1 inserts the measurement probe 3 into the insertion portion 111a. In this case, in the calibration apparatus 11, by the drive unit 113 driving, the rotation plate 112 rotates and the first container 114 moves to a position of the insertion portion 111a. Accordingly, the optical measurement apparatus 1 is able to obtain the internal reflection calibration data.

Subsequently, in the calibration apparatus 11, by the drive unit 113 driving, the rotation plate 112 rotates and the second container 115 moves to the position of the insertion portion 111a. Accordingly, the optical measurement apparatus 1 is able to obtain the reference reflection plate calibration data.

According to the above described sixth embodiment of the present invention, calibration items of the optical measurement apparatus 1 are automatically changeable and thus without performing complicated operations, data of calibration processes are obtainable in one operation.

In the sixth embodiment of the present invention, a positional relation between the measurement probe 3 and the first container 114 or the second container 115 need only be relatively changeable, and for example, the insertion portion 111a may be rotatably provided with respect to a principal plane of the accommodation unit 111b.

Seventh Embodiment

Next, a seventh embodiment of the present invention will be described. In the seventh embodiment, a calibration process is performed in a state in which a calibration apparatus is installed to a measurement probe. Therefore, hereinafter, the configuration of the calibration apparatus according to the seventh embodiment will be described. Configurations that are the same as those of the optical measurement apparatus 1 and the calibration apparatus 4 according to the above described first embodiment will be described being appended by the same reference signs.

Figure 25:
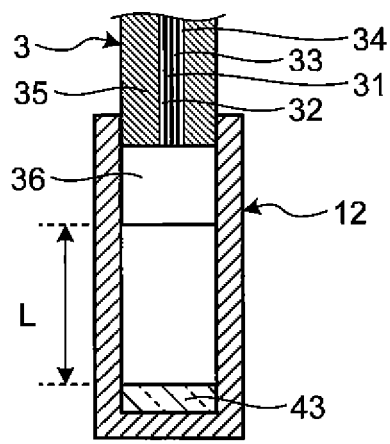
FIG. 25 is a diagram schematically illustrating a cross section of a state in which a measurement probe of an optical measurement apparatus is installed in a calibration apparatus according to a seventh embodiment of the present invention.

FIG. 25 is a diagram that schematically illustrates a cross section of a state in which a measurement probe of an optical measurement apparatus is installed in the calibration apparatus according to the seventh embodiment. A calibration apparatus 12 illustrated in FIG. 25 is a bottomed cuboid and has the reference reflection plate 43 at a position that is away from the measurement probe 3 by the predetermined distance L. Further, the calibration apparatus 12 protects the distal end of the measurement probe 3 from an external force.

The calibration apparatus 12 configured as above is removed from the measurement probe 3 after the optical measurement apparatus 1 obtains the reference reflection plate calibration data. Thereafter, the optical measurement apparatus 1 obtains the internal reflection calibration data by irradiating the illumination light to the container provided with the light absorption member inside thereof.

According to the above described seventh embodiment of the present invention, variation in the predetermined distance L from the measurement probe 3 to the reference reflection plate 43 is preventable and a more accurate calibration process is able to be performed.

In the seventh embodiment of the present invention, when the treatment tool channel 51a of the endoscopic device 51 is usable as a light absorption space, the optical measurement apparatus 1 may obtain the internal reflection correction data inside the treatment tool channel 51a of the endoscopic device 51.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A calibration apparatus configured to obtain a plurality of calibration data during correction of returned light from an object to be measured by an optical measurement apparatus, the optical measurement apparatus including: (i) a measurement probe having an illumination fiber that irradiates illumination light at a wavelength to be measured to the object, and a plurality of detection fibers that are arranged to receive, at different angles, the returned light corresponding to the illumination light reflected and/or scattered by the object to be measured; and (ii) a plurality of detectors configured to detect the returned light respectively received by the plurality of detection fibers, the calibration apparatus comprising:

an insertion portion into which the measurement probe is inserted; and a reference reflection plate that is arranged at a position away from a distal end of the measurement probe by a predetermined distance in a state in which the measurement probe has been inserted in the insertion portion and that has uniform reflectivity of light in a range of the wavelength to be measured in an irradiation plane of the illumination light, wherein:

the plurality of detection fibers include a detection fiber arranged adjacent to the illumination fiber, ends of the illumination fiber and the detection fiber are arranged at a position away from the reference reflection plate by a predetermined distance when the measurement probe is inserted in the insertion portion, and a material forming the reference reflection plate has a scattering mean free path that is greater than a spatial coherence length at the predetermined distance.

2. The calibration apparatus according to claim 1, wherein the material forming the reference reflection plate has the scattering mean free path that is greater than twice the spatial coherence length and has an anisotropic parameter that is equal to or less than 0.85.

3. The calibration apparatus according to claim 1, wherein the material forming the reference reflection plate has the scattering mean free path that is approximately equal to twice the spatial coherence length and has an anisotropic parameter is greater than 0.85.

4. The calibration apparatus according to claim 1, further comprising:

a drive unit that moves the reference reflection plate towards the distal end of the measurement probe when the optical measurement apparatus obtains the calibration data.

5. The calibration apparatus according to claim 1, further comprising:
an accommodation portion that accommodates the reference reflection plate, wherein the insertion portion and the accommodation portion are connected to each other or arranged changeably between each other.

6. The calibration apparatus according to claim 5, wherein
the insertion portion has a light absorption portion provided with, on an inner surface thereof, a light absorption member that absorbs light, the light absorption portion being tubular, and
the plurality of calibration data are:
reference reflection plate calibration data when measurement is performed in the accommodation portion; and
internal reflection calibration data of the measurement probe when measurement is performed in the insertion portion.

7. The calibration apparatus according to claim 1, wherein the insertion portion:
has an opening at an end thereof,
is bottomed and tubular,
has, on an inner surface at a position near an insertion opening through which the measurement probe is inserted, a light absorption portion provided with a light absorption member that absorbs light, and
has the reference reflection plate provided on a bottom portion thereof.

8. The calibration apparatus according to claim 7, wherein the insertion portion is bent.

9. The calibration apparatus according to claim 1, further comprising:
a first container provided inside thereof with an optical absorption member that absorbs light;
a second container that accommodates the reference reflection plate;
a change portion that changes, with respect to the insertion portion, positions of the first container and the second container; and
a change drive unit that drives the change unit.

10. A calibration method of obtaining calibration data using a calibration apparatus with respect to an optical measurement apparatus that includes: a measurement probe having an illumination fiber that irradiates to an object to be measured illumination light including at least light of wavelength to be measured and a plurality of detection fibers that receive, at different angles, returned light of the illumination light reflected and/or scattered by the object to be measured; and a plurality of detection units that detect the returned light respectively received by the plurality of detection fibers, the calibration method comprising:
a first step of obtaining data for internal reflection calibration of the measurement probe detected by the detection units when the measurement probe is caused to irradiate the illumination light to an insertion portion that is provided, inside the calibration apparatus, with a light absorption member that absorbs light; and
a second step of obtaining reference reflection plate calibration data detected by the detection units when the measurement probe irradiates the illumination light to a reference reflection plate in the calibration apparatus, the reference reflection plate being arranged at a position away from a distal end of the measurement probe by a predetermined distance and having uniform reflectivity of light over a range of the wavelength to be measured in an irradiation plane of the illumination light,
wherein a material forming the reference reflection plate has a scattering mean free path that is greater than a spatial coherence length at the predetermined distance.

* * * * *